(12) United States Patent
Schmotzer et al.

(10) Patent No.: US 7,306,609 B2
(45) Date of Patent: Dec. 11, 2007

(54) FEMORAL SLIDEWAY

(75) Inventors: Hans Schmotzer, Kölliken (CH); Peter Schuler, Karlsruhe (DE); Udo Malzer, Karlsruhe (DE)

(73) Assignee: Plus Orthopedics AG (CH)

( * ) Notice: Subject to any disclaimer, the term of this patent is extended or adjusted under 35 U.S.C. 154(b) by 54 days.

(21) Appl. No.: 10/616,102

(22) Filed: Jul. 9, 2003

(65) Prior Publication Data

US 2004/0059426 A1 Mar. 25, 2004

Related U.S. Application Data

(62) Division of application No. 09/517,674, filed on Mar. 2, 2000, now abandoned.

(30) Foreign Application Priority Data

Mar. 2, 1999 (DE) .......................... 299 03 766 U
Apr. 16, 1999 (DE) .......................... 299 06 909 U

(51) Int. Cl.
*A61B 17/56* (2006.01)
(52) U.S. Cl. ...................... 606/88; 623/20.31
(58) Field of Classification Search ............. 623/20.14, 623/20.15, 20.31, 20.35, 901, 914, 923, 908; 606/88
See application file for complete search history.

(56) References Cited

U.S. PATENT DOCUMENTS

| 3,816,855 | A | 6/1974 | Saleh ....................... 623/20.31 |
| 4,944,756 | A | 7/1990 | Kenna |
| 5,116,338 | A | 5/1992 | Poggie et al. |
| 5,326,361 | A | 7/1994 | Hollister ................... 623/20.31 |
| 5,549,684 | A | 8/1996 | Amino et al. |
| 5,549,688 | A | 8/1996 | Ries et al. ................ 623/20.35 |
| 5,688,280 | A | 11/1997 | Booth, Jr. et al. |
| 5,776,201 | A | 7/1998 | Colleran et al. ......... 623/20.31 |
| 5,810,831 | A | 9/1998 | D'Antonio |
| 6,364,911 | B1 | 4/2002 | Schmotzer et al. |

FOREIGN PATENT DOCUMENTS

| DE | 299 06 909 | 1/2000 |
| EP | 0 707 839 A1 | 4/1996 |
| EP | 0 765 645 A2 | 4/1997 |
| EP | 1 033 117 A3 | 1/2003 |
| WO | WO 94/26212 | 11/1994 |
| WO | WO 95/35074 | 12/1995 |
| WO | WO 97/30661 | 8/1997 |

*Primary Examiner*—Brian E. Pellegrino
(74) *Attorney, Agent, or Firm*—Knobbe Martens Olson & Bear, LLP

(57) ABSTRACT

A femoral slideway and a femoral slideway/femur-size template combination is employed to create an installed knee prosthesis that creates a reduced amount of stress in the collateral ligaments relative to previous prostheses. In one embodiment, the reduced stress is achieved by employing a femoral slideway/femur-size template combination which results in installation of a femoral slideway which has a smaller dorsal-ventral dimension than a corresponding dimension of the femur prior to resection.

26 Claims, 4 Drawing Sheets

FEMORAL SLIDEWAY

CROSS REFERENCE TO RELATED APPLICATIONS

Figure 1:
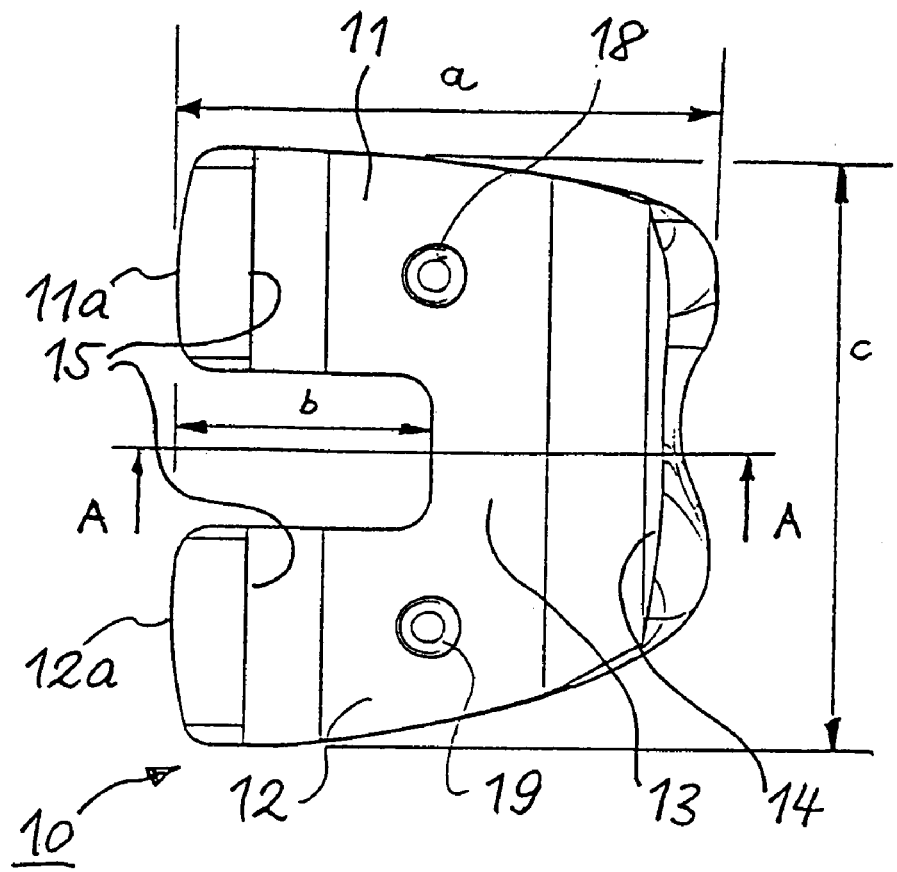

This Application is a Divisional of U.S. patent application Ser. No. 09/517,674, filed on Mar. 2, 2000 now abandoned, the entire contents of which is incorporated herein by reference. This Application also relates to German Patent Applications DE 29906909.5, filed Apr. 16, 1999, and DE 299 03 766.5, filed on Mar. 2, 1999.

BACKGROUND

1. Field of the Invention

The invention relates to a femoral slideway, and more specifically to a femoral slideway/femur-size template arrangement and a knee endoprosthesis system with such a femoral slideway.

2. Description of the Related Art

A femoral slideway of this kind is disclosed, for example, in the German patent DE 40 41 002 C2. In the surgical technique customarily used for knee-joint replacement by means of such a femoral slideway, an equal amount of bone is removed from the two condyles of the femur, so that the anterior or ventral cut is parallel to the posterior or dorsal cut. When the implant is in the position thus defined, the axis of rotation of the implant no longer coincides with the axis specified by the arrangement of the collateral ligaments, and this position is not anatomical inasmuch as when flexed, the implant is seated either too tightly on the medial side or too loosely on the lateral side.

The remedy that was recommended some time ago, namely an outward rotation of the cutting guide such that in the posterior region less bone is removed laterally than medially, whereas anterior-laterally more bone is removed than on the anterior-medial side, also presents disadvantages, which the construction of the femoral slideway proposed in DE 197 16 879 A1 of the applicant is designed to eliminate. The crux of this solution is to rotate the anterior or ventral cut in the transverse plane.

However, this more recent solution also requires improvement with respect to optimizing the joint function in cooperation with the collateral ligaments in particular, especially in order to reduce the load imposed thereon.

It is thus the object of the invention to disclose a femoral slideway with further improved function, as well as a knee endoprosthesis system that can be efficiently constructed and employed and has such a femoral slideway as its essential element, and finally an advantageous arrangement comprising femoral slideway and femur-size template.

This object is achieved in its first, foremost aspect by a femoral slideway with the features described in the present application.

The invention includes the essential idea that it is advantageous to prepare for a knee-joint replacement by resecting more bone from the femur dorsally than is replaced by the implant (the femoral slideway). The "diminution" of the femoral slideway thus brought about in the dorsal region, in comparison to the original dimensions of the (resected) condyles or to a femoral slideway fitted in the conventional manner, produces an effective reduction of the turning radius of the tibial plate belonging to the prosthesis system and hence reduces the load on the collateral ligaments.

The decrease in the dimensions of the femoral slideway measured between the outermost, dorsoventrally opposed points on the condyle shell surfaces, in comparison to the previously customary dimensioning, is preferably in the range between 2 and 5%. This is achieved by constructing the associated femoral slideway/femur-size template arrangement in such a way that the distance separating one or more pegs on the femoral slideway from its dorsal sliding surface is smaller by 5-15%, in particular by about 10%, than the corresponding distance by which bores in the femur-size template for positioning the pegs are separated from the contact surface that is to be apposed to the dorsal condyle surfaces of the femur.

The distance between the dorsal sliding surfaces and the one or more pegs on the inside of the femoral slideway is preferably in the range between 24 and 34 mm and in particular is 29 mm, the chosen value advantageously being kept constant in a knee endoprosthesis system for covering a relevant joint-size range.

As noted above, the femoral slideway/femur-size template arrangement is constructed in such a way that the distance between one or more pegs on the femoral slideway and its dorsal sliding surface is smaller than the corresponding distance between bores in the femur-size template and the contact surface of the template by 5-15%. and in particular about 10%. Stated differently, the corresponding distance between bores in the femur-size template and the contact surface of the template is larger by 5-15%, an in particular about 10%. than the distance between one or more pegs on the femoral slideway and its dorsal sliding surface. Accordingly, the distance between the bores in the femur-size template and the contact surface of the template can be between 26.4 mm and 37.4 mm (i.e., 10% larger than the range of 24 mm to 34 mm between the dorsal sliding surface and the one or more pegs of the femoral slideway). In another embodiment, the distance between the bores in the femur-size template and the contact surface of the template can be about 32 mm (i.e., about 10% larger than a distance of 29 mm between the dorsal sliding surface and the one or more pegs of the femoral slideway). In yet another embodiment, the distance between the bores in the femur-size template and the contact surface of the template can be between 30.45 mm and 33.35 mm (i.e., 5%-15% larger than a distance of 29 mm between the dorsal sliding surface and the one or more pegs of the femoral slideway).

Another distinguishing feature of the proposed femoral slideway is that particular dimensions maintain a largely constant relationship to one another, regardless of the size of the actual prosthesis. For instance, the ratio a:c between the maximal dorsoventral extent and the maximal lateral extent of the femoral slideway is about 0.9±0.02. The patellar pit formed between the condyle shells preferably has a depth b, measured from the dorsalmost point on the condyle shells, such that its ratio b:a to the maximal dorsoventral extent of the femoral slideway is in the range between 0.4 and 0.5, in particular is 0.44.

The patellar pit is thus lengthened in the dorsal direction, as a result of which the patella can be supported over a large area throughout its entire functional range of flexion.

This elongation of the patellar pit, which furthermore increases in accordance with the anatomy in implants of all sizes, allows for the fact that the patello-femoral contact surface in conventional femoral slideways has a relatively small bearing area. That is, in the region in which the patella leaves the trochlea and enters the intercondylar fossa, conventional femur components provide support only in the peripheral regions.

Furthermore, in the proposed femoral slideway the condyle shells are somewhat more strongly rounded in cross section (coronal section) than is the case in conventional femoral slideways. This modification was undertaken in the interest of improving the fit to the special tibia insert that belongs to a knee endoprosthesis system, but which is not within the scope of the invention.

The back surface of the femoral slideway, in one advantageous embodiment, bears a two-component Ti coating produced in a vacuum plasma procedure, consisting of a relatively thin, dense base layer and a severalfold thicker, open-pored cover layer. The dense base layer allows the femoral slideway, which for example consists of CoCrMo, to become completely sealed to the bone and, because it makes contact with the substrate over a large area, increases the stability of adhesion.

The open-pored and very rough surface of the cover layer provides ideal conditions for the growth of bony substance onto and into the carriage, producing a quasi "3-D interlocking" that can transmit pulling forces as well as pressure and transverse forces.

Figure 2:
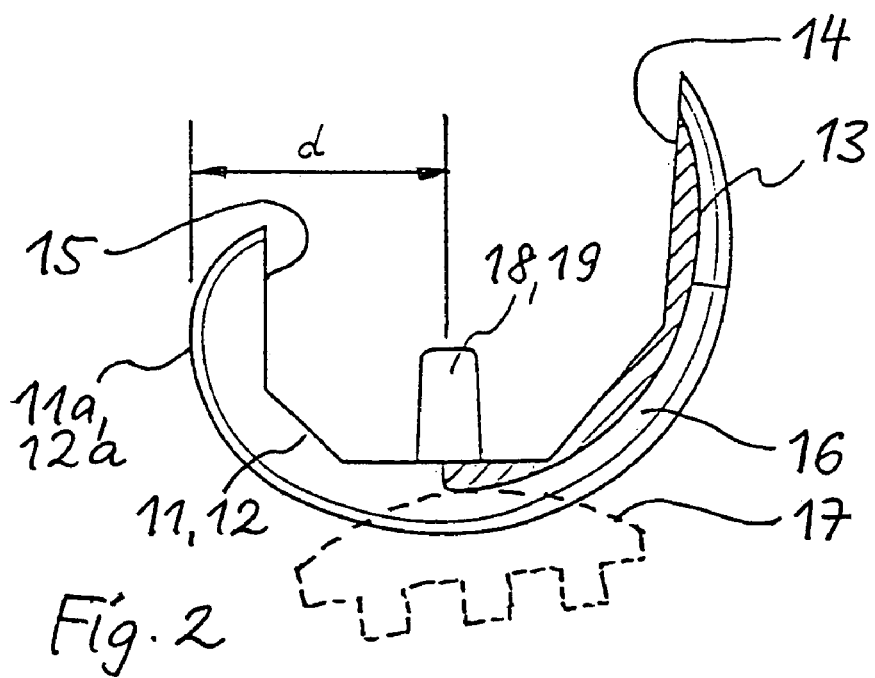
Figure 3:
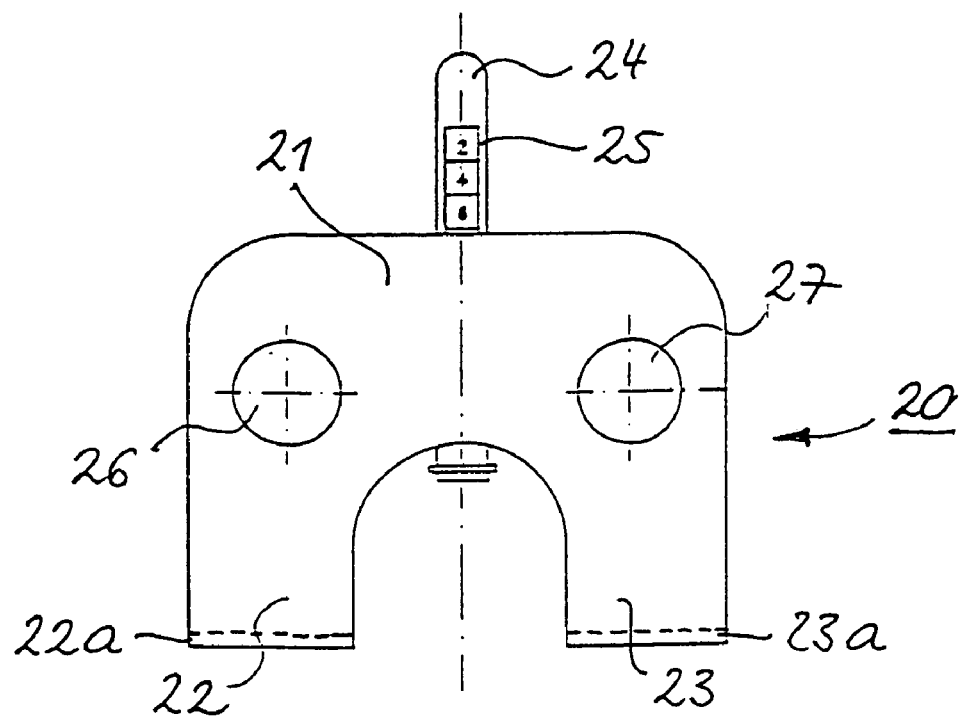
Figure 4:
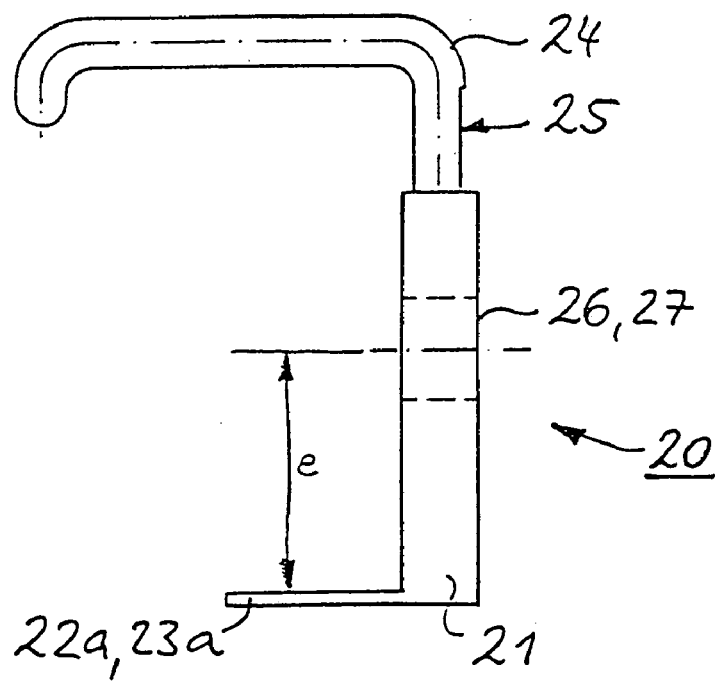
Figure 5A:
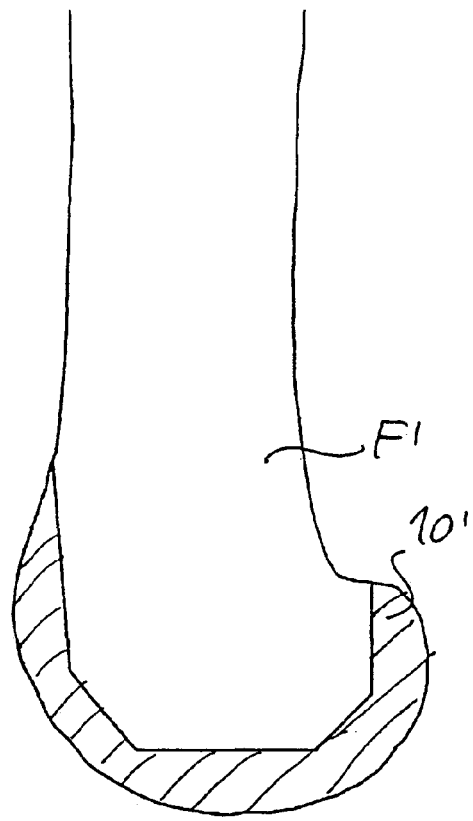
Figure 5B:
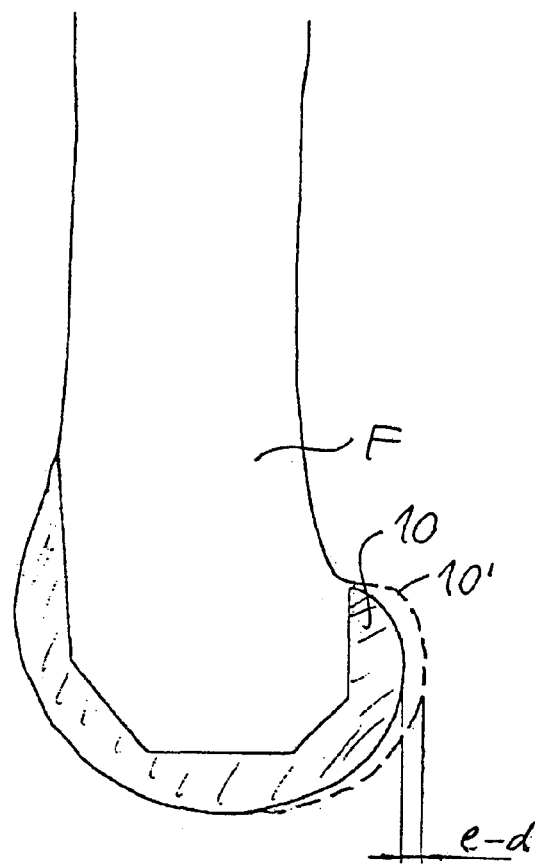
Figure 6A:
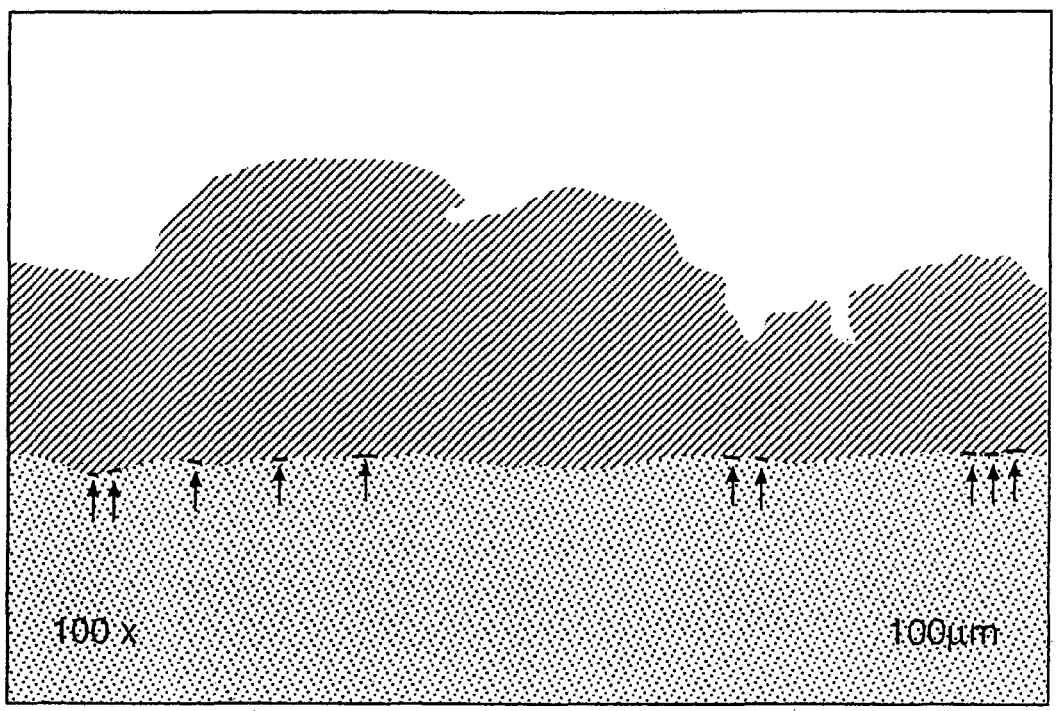
Figure 6B:
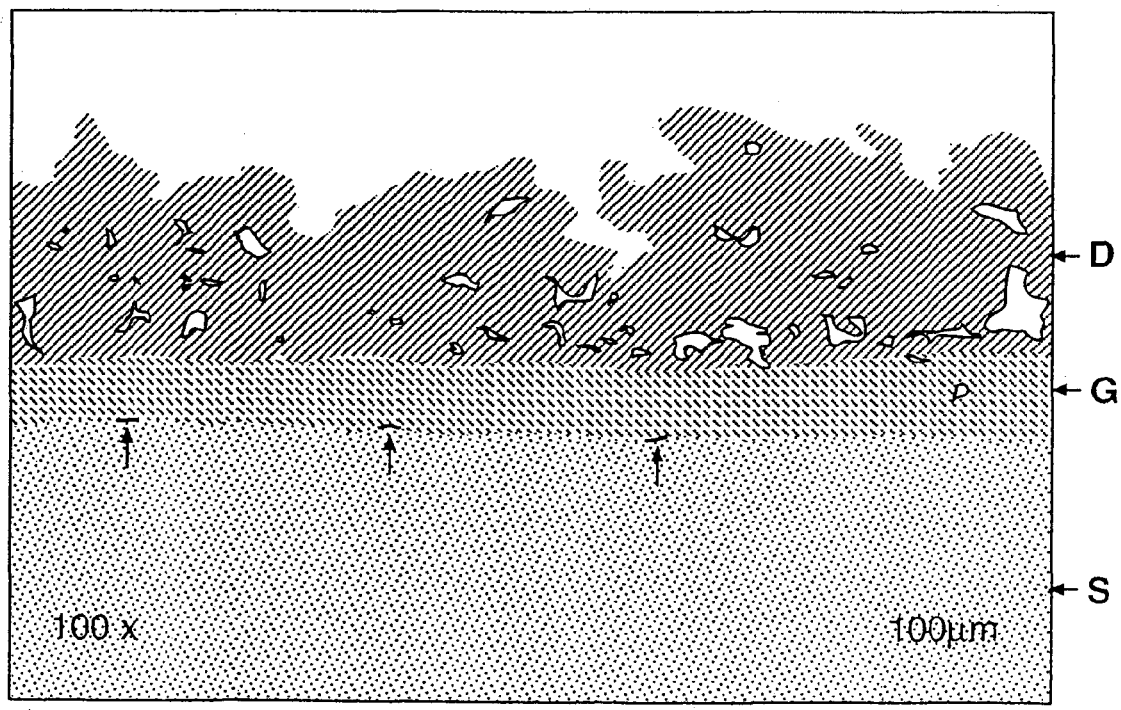

Additional advantages and useful features of the invention will be apparent from the subordinate claims and the following description of an exemplary embodiment with reference to the figures, wherein BRIEF DESCRIPTION Of THE DRAWINGS FIG. 1 is a view (from proximal) of a femoral slideway according to one embodiment of the invention, FIG. 2 shows the femoral slideway according to FIG. 1 in median section (sagittal section), FIG. 3 is a plan view of an embodiment of a femur-size template, FIG. 4 is a side view of the latter, FIGS. 5a, 5b show a conventional arrangement of a femoral slideway on a femur in comparison to an arrangement proposed here, and FIGS. 6a, 6b show scanning electron micrographs of a cross section of a conventional layered structure and of an embodiment of the layered structure proposed here for the back-surface coating of a femoral slideway.

DETAILED DESCRIPTION Of The PREFERRED EMBODIMENTS

In FIGS. 1 and 2 the femur component 10, called a femoral slideway, of a knee endoprosthesis is shown. The femoral slideway 10 comprises two convexly curved condyle shells 11, 12 and a patellar shield 13, which connects the two condyle shells 11, 12 rigidly to one another.

The condyle shells 11, 12 and the patellar shield 13 in their interiors define anterior and posterior fitting surfaces 14, 15 that correspond to a femoral ventral and dorsal cut, respectively, and are associated with a ventral and a dorsal saw-cut surface produced at the distal end of the femur when the latter was resected for fitting of the femoral slideway. The convex outer shape of the condyle shells 11, 12 specifies dorsal sliding surfaces 11a, 12a in the posterior region, over which the corresponding surfaces of the tibia insert slide when the knee endoprosthesis is flexed. The patellar shield 13, which is recessed with respect to the convex outer surfaces of the condyle shells 11, 12, defines a so-called patellar pit 16, within which there is supported a patella component 17 of the knee endoprosthesis, which is indicated by a dashed outline in FIG. 2 and does not belong to the femoral slideway 10.

To assist anchoring and central placement of the femoral slideway 10 on the femur, on the inner surface of the femoral slideway two pegs 18, 19 are formed, the long axis of which is substantially parallel to the posterior fitting surface 15. These pegs project into holes in the femur, which have been drilled in the appropriate positions with the aid of a corresponding drilling template (see below), and this engagement gives the attachment of femoral slideway to bone greater stability than is provided by the fitting surfaces alone.

To ensure that the the femoral slideway will function optimally as a replacement for destroyed sliding surfaces on the femur, the construction must reflect as accurately as possible the anatomical arrangements and dimensions, but also within the scope of the invention includes a specific modification that will now be explained.

One of the relevant dimensions of the femoral slideway 10 is the maximal anterior-posterior or dorsoventral extent of the condyle shells 1, 12, a distance labelled a in FIG. 1. Another relevant dimension is the maximal lateral extent of the femoral slideway, i.e. the distance between the most lateral point on the lateral condyle shell 11 and the most medial point on the medial condyle shell 12, which in FIG. 1 is labelled c. Also significant is the distance from the outermost posterior point on the dorsal sliding surfaces 11a, 12a of the condyle shells 11, 12 to the posterior bounding edge of the patellar shield 13, which in FIG. 1 is labelled b. A final significant distance is that between the outermost posterior points on the dorsal sliding surfaces 11a, 12a and the long axis of the pegs 18, 19 (which lie in one and the same coronal plane), labelled d in FIG. 2. In the exemplary embodiment described here, the ratio a:c is 0.9 and the ratio b:a is 0.44. On grounds of biomechanics and surgical technique, it has proved useful to make the distance d (between sliding surface and peg axis) uniform for all sizes of femoral slideway used in a knee endoprosthesis system. In the present case, this distance is 29 mm.

To determine the correct femoral slideway size, a femur-size template 20 shown in FIGS. 3 and 4 is used. This comprises a basic part 21 with two flanks 22 and 23, each of which ends in a contact section 22a, 23a that is bent at a right angle and is apposed to the condyles of a femoral bone that is to be fitted with a femoral slideway (FIGS. 1 and 2).

In the middle of the basic part 21 a measurement tongue 24, bent at an angle in two places, is mounted so that it can be displaced in a direction perpendicular to the plane in which the contact sections 22a, 23a lie. The measurement tongue 24 is marked with a scale 25, which indicates the maximal anterior-posterior extent of the head of the femur, i.e. the condyles, and thus indicates to the doctor the required size of the implant. In the basic part 21 of the femur-size template 20 two peg-hole bores 26, 27 are provided, which—in accordance with a supplementary drilling-template function of the femur-size template—assist the positioning of peg-holes in the femur so that they correspond to the pegs 18, 19 of the femoral slideway 10 as shown in FIG. 1. The axes of the peg-hole bores 26, 27 are separated by a distance e from the contact surfaces of the contact sections 22a, 23a. This distance—along with the distance d between the sliding surfaces and pegs on the femoral slideway 10 itself (cf. FIG. 2)—is an additional relevant dimension in the concrete implementation of a knee endoprosthesis, for the following reason:

So that the above-mentioned peg-holes—which serve not only to position the implant but also to position the cutting guides used to produce the various saw cuts on the femur—can be drilled into the bone, drill bushes (not shown) are inserted into the peg-hole bores 26, 27.

It has proved advantageous, in particular from the viewpoint of reducing the load on the collateral ligaments during flexion of the artificial knee joint, to resect more bone dorsally on the femur than will be replaced there by the thickness of the dorsal parts of the condyle shells. For this reason the distance e is made larger than the corresponding distance d (FIG. 2). In the preferred embodiment the relative distance reduction, i.e. the quantity (e−d)/d, is about 10%.

The effect thus achieved can be seen in FIG. 5, where a sketch representing the conventional way of attaching a femoral slideway 10' to a femur F', shown in FIG. 5a, is compared with the representation in FIG. 5b of the arrangement proposed here. The anterior-posterior extent of the femoral slideway 10 in FIG. 5b, mounted on a femur F resected further in the dorsal region, is smaller by the amount (e−d) than in the conventional implant 10'.

Because the distance e is permanently specified by the femur-size template, which is used for all implants regardless of their size, and according to what has been stated above the distance d in the embodiment of the femoral slideway is preferably kept constant for all implant sizes, the geometric relations will be slightly different for implants of different sizes. This is acceptable, however, in view of the advantages for manufacture and manipulation that such a system brings.

FIG. 6b shows—in comparison to a conventional femur-carriage coating as shown in FIG. 6a—the appearance in the scanning electron microscope of a cross section through a two-component titanium-coating construction consisting of a dense base layer G, about 50 µm thick, and an open-pored cover layer D averaging about 250 µm thick, on a CoCrMo substrate S. Although the thickness and average roughness of the coating according to FIG. 6b, which is applied by a vacuum plasma process, are comparable to those of the known, sprayed-on coating according to FIG. 6a, it should be emphasized that the former has a more open-pored structure and a considerably reduced number of interface defects (indicated in both pictures by vertical arrows).

Implementation of the invention is not limited to the exemplary embodiment described above, but can also incorporate modifications, which in particular include departures from the specified dimensions and ratio values.

LIST OF REFERENCE NUMERALS

| | |
|---|---|
| 10, 10' | Femoral slideway |
| 11, 12 | Condyle shells |
| 11a, 12a | Dorsal sliding surfaces |
| 13 | Patellar shield |
| 14 | Anterior fitting surface |
| 15 | Posterior fitting surface |
| 16 | Patellar pit |
| 17 | Patella component |
| 18, 19 | Peg |
| 20 | Femur-size template |
| 21 | Basic part |
| 22, 23 | Flanks |
| 22a, 23a | Contact sections |
| 24 | Measurement tongue |
| 25 | Scale markings |
| 26, 27 | Peg-hole bores |
| a, b, c, d, e | Distances |
| A-A | Plane of section |
| D | Cover layer |
| F, F' | Femur (shaped) |
| G | Base layer |
| S | Substrate |

What is claimed is:

1. A method of preparing a lower extremity of a femur and implanting a femoral slideway thereon, the method comprising:

providing a femoral slideway having at least one peg adapted for insertion into a hole in the femur;

locating a point on a lower extremity of a femur, said point being located at a pre-determined distance from a plane tangent to dorsalmost points of lateral and medial condyles of the femur, the pre-determined distance defined by a template having a permanently specified distance between a bore on a support part and a contact surface on a flank of the template, the support part and flank defined as a single piece, the contact surface configured to engage at least one of the dorsalmost points of the lateral and medial condyles of the femur;

drilling a hole at said point; and selecting a femoral slideway having a dimension defined by a perpendicular distance between a longitudinal axis of a peg extending from the slideway and a plane tangent to a dorsal sliding surface farthest away from the peg;

wherein said pre-determined distance is larger than said dimension.

2. The method of claim 1, further comprising resecting bone material from the femur and fitting the slideway onto the femur by inserting the peg into the hole.

3. The method of claim 1, wherein said pre-determined distance is about 5% to about 15% larger than said dimension.

4. The method of claim 3, wherein said pre-determined distance is about 10% larger than said dimension.

5. The method of claim 1, wherein said locating is performed before said drilling.

6. The method of claim 1, wherein said selecting a femoral slideway further comprises selecting a slideway with a dimension between a dorsal sliding surface and a ventral sliding surface which is a previously-determined percent of a distance between a dorsal-most condylar surface and a ventral-most condylar surface of the femur before said resecting.

7. The method of claim 6, wherein said percent is about 2 to 5%.

8. The method of claim 1, wherein selecting further comprises selecting a femoral slideway from a group of slideways, wherein all of the slideways in said group have substantially equal peg-to-sliding-surface dimensions as defined by a perpendicular distance between a longitudinal axis of a peg extending from the slideway and a plane tangent to a dorsal sliding surface furthest away from the peg; and wherein each slideway in said group has a different dorsal condyle-to-ventral condyle distance.

9. The method of claim 1, wherein the bore and the contact surface are defined on a unitary part of the template.

10. A method of preparing a lower extremity of a femur for implantation of a femoral slideway, said method comprising:

determining a location for a hole to be drilled in a lower surface of a femur bone by indicating a point at a previously-determined distance from a dorsal-most point of a condyle of said femur;

wherein said previously-determined distance is 5 to 15% larger than a distance between a peg and a dorsal sliding surface of the femoral slideway to be implanted on said femur bone;

drilling the hole in a lower surface of a femur bone at said point;

resecting bone material from said femur, wherein said resecting includes removing more bone material from a dorsal side of the femur than will be replaced by the slideway to allow for a reduction of the distance between the peg and a center of the turning radius of the dorsal portion of the slideway compared to the unresected femur to reduce a load on ligaments attached to the femur; and implanting the slideway on the femur by inserting the peg into the hole.

11. The method of claim 10, wherein said previously-determined distance is about 10% larger than a distance between a peg and a dorsal sliding surface of the femoral slideway to be implanted on said femur bone.

12. The method of claim 11, wherein the distance between the peg and the dorsal sliding surface of the femoral slideway is between about 24 mm and about 34 mm.

13. The method of claim 12, wherein the distance between a peg and a dorsal sliding surface of the femoral slideway is about 29 mm.

14. The method of claim 11, wherein said previously-determined distance is between 26.4 mm and 37.4 mm.

15. The method of claim 14, wherein the previously-determined distance is about 32 mm.

16. The method of claim 10, wherein said previously-determined distance is between 30.45 mm and 33.35 mm.

17. The method of claim 10, wherein resecting bone material from the dorsal side of the femur includes resecting an equal amount of bone from the medial and lateral posterior condyles.

18. A method of implanting a femoral slideway on a femur, said method comprising:

providing a slideway comprising two convexly curved condyle shells rigidly connected to one another anteriorly by a patellar shield, wherein outer surfaces of the condyle shells define dorsal sliding surfaces of the femoral slideway, wherein the femoral slideway has on an inner surface at least one peg, wherein between a long axis of the peg or pegs and a point on a dorsal sliding surface furthest away therefrom a sliding-surface-to-peg distance is defined, and wherein an overall extent of the femoral slideway in an anterior-posterior direction is smaller than a corresponding original overall extent of the condyles of a femur to which the femoral slideway is fitted;

resecting bone material from a femur, wherein said resecting includes removing more bone material from a dorsal side of the femur than is replaced by the slideway;

providing at least one hole in said femur to receive said at least one peg of said slideway and to secure and locate said slideway on said femur, the position of said at least one hole being a pre-determined distance from a plane tangent to dorsalmost points of lateral and medial condyles of the femur, the pre-determined distance defined by a femur-size template having a permanently specified distance between a bore on a support part and a contact surface on a flank of the template, the support part and the flank defined as a single piece, the contact surface configured to engage at least one of the dorsalmost points of the lateral and medial condyles of the femur; and fitting said slideway onto said femur.

19. The method of claim 18, wherein said resecting includes removing about 10% more bone material from the dorsal side of the femur than is replaced by the slideway, as measured linearly between said holes and a dorsalmost surface of said femur.

20. The method of claim 18, further comprising positioning the femur-size template on said femur to determine the position of said at least one hole in the femur.

21. The method of claim 20, wherein said femur-size template comprises a dorsal condyle-engaging surface and at least one bore separated by a pre-determined distance.

22. The method of claim 21, wherein said pre-determined distance is about 5 to 15% larger than a perpendicular distance between said at least one peg and said dorsal sliding surfaces.

23. The method of claim 22, wherein said pre-determined distance is about 10% larger than a perpendicular distance between said at least one peg and said dorsal sliding surfaces.

24. The method of claim 18, wherein resecting bone material from the dorsal side of the femur includes resecting an equal amount of bone from the medial and lateral posterior condyles.

25. A method of preparing a lower extremity of a femur and implanting a femoral slideway thereon, the method comprising:

providing a femoral slideway having at least one peg adapted for insertion into a hole in the femur;

locating a point on a lower extremity of a femur, said point being located at a pre-determined distance from a plane tangent to dorsalmost points of lateral and medial condyles of the femur, the pre-determined distance defined by a template having a permanently specified distance between a bore on a support part and a contact surface on a flank of the template, the support part and flank permanently connected to each other, the contact surface configured to engage at least one of the dorsalmost points of the lateral and medial condyles of the femur;

drilling a hole at said point; and selecting a femoral slideway having a dimension defined by a perpendicular distance between a longitudinal axis of a peg extending from the slideway and a plane tangent to a dorsal sliding surface furthest away from the peg;

wherein said pre-determined distance is larger than said dimension.

26. The method of claim 25, wherein the previously-determined distance is 5 to 15% larger than the distance between the peg and the dorsal sliding surface of the femoral slideway to be implanted on the femur bone.

* * * * *